United States Patent
Yavitz

[11] Patent Number: 5,980,497
[45] Date of Patent: *Nov. 9, 1999

[54] MEMBRANE SHIELD FOR EYES

[76] Inventor: Edward Q. Yavitz, 3828 Spring Creek Rd., Rockford, Ill. 61114

[ * ] Notice: This patent is subject to a terminal disclaimer.

[21] Appl. No.: 08/906,797

[22] Filed: Aug. 5, 1997

Related U.S. Application Data

[63] Continuation-in-part of application No. 08/867,122, Jun. 2, 1997, Pat. No. 5,740,550, which is a continuation-in-part of application No. 08/709,473, Sep. 5, 1996, abandoned
[60] Provisional application No. 60/013,479, Mar. 15, 1996.
[51] Int. Cl.⁶ .............................. A61M 35/00; A61F 9/04
[52] U.S. Cl. ................... 604/294; 604/304; 604/302; 128/858; 2/15
[58] Field of Search .................. 604/294, 295, 604/300–302; 602/52, 54, 74; 128/858, 857, 887, 888; 2/15, 11, 426, 440, 442, 206; 351/62, 178, 41, 110

[56] References Cited

U.S. PATENT DOCUMENTS

| | | |
|---|---|---|
| 2,143,856 | 1/1939 | Biggs . |
| 2,896,615 | 7/1959 | Szigeti . |
| 3,068,863 | 12/1962 | Bowman . |
| 3,092,103 | 6/1963 | Mower . |
| 3,300,786 | 1/1967 | Rosenvold et al. . |
| 3,952,735 | 4/1976 | Wirtschafter et al. . |
| 3,973,561 | 8/1976 | Kane . |
| 4,473,370 | 9/1984 | Weiss . |
| 4,682,371 | 7/1987 | Heltman . |
| 4,709,695 | 12/1987 | Kohn et al. . |
| 4,793,003 | 12/1988 | Riedel et al. . |
| 4,862,902 | 9/1989 | Goffman . |
| 4,867,146 | 9/1989 | Krupnick et al. . |
| 4,969,472 | 11/1990 | Langley et al. . |
| 4,979,811 | 12/1990 | Boyer . |
| 5,661,850 | 9/1997 | Martinique . |
| 5,700,238 | 12/1997 | Hyson ........................................ 602/74 |
| 5,740,550 | 4/1998 | Yavitz ............................................ 2/15 |

OTHER PUBLICATIONS

Brochure, Pro–ophta™ Adhesive Eye Dressing, Type S, No. 95574.

*Primary Examiner*—Ronald Stright
*Assistant Examiner*—David J. Cho
*Attorney, Agent, or Firm*—Fletcher, Yoder & Van Someren

[57] ABSTRACT

A membrane shield for application over the eye of a wearer to retain moisture. The moisture shield includes a window that can be made of a transparent plastic. A collar is connected to the perimeter of the window such that the collar extends outwardly from the window. An adhesive layer, such as an adhesive gel, is applied to the collar to permit the moisture shield to be adhered to the wearer's face about the eye. A vapor distribution element is attached to the membrane shield to expose the eye to a desired substance or substances, such as water or medication.

20 Claims, 3 Drawing Sheets

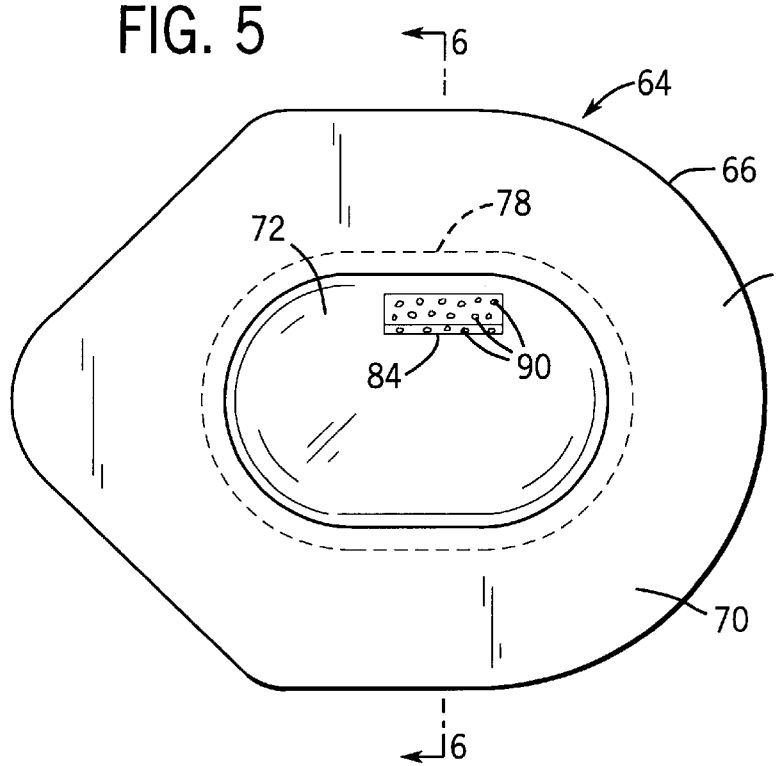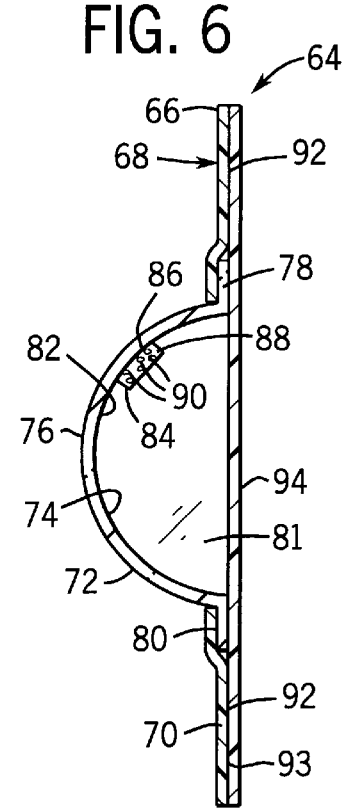

MEMBRANE SHIELD FOR EYES

This document is a continuation-in-part of application Ser. No. 08/867,122 now U.S. Pat. No. 5,740,550, entitled Membrane Shield for eyes, filed on Jun. 2, 1997, which is a continuation-in-part of patent application Ser. No. 08/709,473, entitled Membrane Shield for Eyes, filed on Sep. 5, 1996, now abandoned, which was based on and claimed priority of Provisional Application Ser. No. 60/013,479 entitled Membrane Shield for Eyes, filed on Mar. 15, 1996.

FIELD OF THE INVENTION

The present invention relates generally to a device for protecting mammalian eyes, and particularly to a membrane shield that may be adhered to the face of a person about the eye to retain and/or supplement moisture in the eye.

BACKGROUND OF THE INVENTION

When eyes are exposed to the elements, such as heat, cold or dry air, the moisture in the membranes of the eyes tends to evaporate, leaving the person with uncomfortably dry eyes. Retaining moisture is particularly difficult for the elderly and for persons with certain eye disorders. Additionally, it is often helpful to retain a high level of moisture in the membranes of the eyes following certain types of eye surgeries.

Eyes also are susceptible to dirt, bacteria, and other particles that become lodged therein. Dirt and bacteria are especially problematic following certain eye surgeries. They are also a problem in environments where the air is recirculated, as for example, in airplanes.

Standard goggles are currently used to protect the eyes. Goggles are secured over the eyes by a strap that wraps around the wearers head If the strap is too loose, the goggles will not stay in place. On the other hand, if the strap is tightly fastened, the user may complain that the goggles are uncomfortable. Another problem with goggles is their bulk which makes them conspicuous when worn. Because they take up more space, bulky goggles are also difficult to store in a purse or a pocket.

Another product sold to protect eyes, as well as to treat dry eyes, is the PRO-OPHTHA S™ adhesive eye dressing, product no. 95574 distributed by Visitec Company, located in Sarasota, Fla. This product has a clear, hard plastic center with a porous flap extending outwardly from the hard plastic center. The porous flap includes an adhesive applied to one surface to permit adherence of the flap to the face of a wearer surrounding one of the wearer's eyes. Due to the porous, vapor permeable nature of the flap, moisture, e.g., water vapor, can still escape from the region surrounding the wearer's eye, and bacteria has access to the eye. For serious dryness problems and for proper therapy following certain eye surgeries, the eye should be separated from the environment by a moisture barrier.

Another product that has been distributed by Solan Opthalmic Products of Jacksonville, Florida is the Guibor EXPO BANDAGE® Eye Bubble eye cover which includes a clear, stiff plastic bubble surrounded by a plastic flap. The flap includes adhesive applied to one surface to permit the product to be adhered over the wearer's eye. However, the bubble is inflexible and the flap is relatively narrow which can lead to gaps between the flap and the wearer's face, thereby providing a less secure moisture barrier.

Both of the above-described products work well for some procedures, but in many applications, it would be advantageous to create a more secure moisture barrier that could supplement the moisture in the eye or medicate the eye. In other situations, it would be advantageous to incorporate vision correction lenses into the eye shield.

The present invention addresses the drawbacks of existing eye protection devices.

SUMMARY OF THE INVENTION

The present invention, according to a preferred embodiment, features a delivery system for delivering a desired substance to an individual's eye over an extended period of time. The delivery system comprises a window having an interior surface, an exterior surface and a perimeter region. A collar extends outwardly from the perimeter region to facilitate mounting to an individual's face about the eye. An absorbent pad is disposed adjacent the interior surface. The adsorbent pad is sufficiently porous to absorb a desired substance prior to mounting the delivery system over the eye.

According to another aspect of the invention, a moisture shield is provided for application to a mammalian face to retain moisture in a mammalian eye. The moisture shield comprises a window having an interior surface, an exterior surface and a perimeter region. An attachment collar extends outwardly from the perimeter region, and an adhesive layer is disposed on the attachment collar. The adhesive layer facilitates attachment of the moisture shield to the mammalian face. Additionally, a substance delivery element is disposed at least partially between the interior surface of the window and the mammalian eye when the moisture shield is attached to the mammalian face.

According to another aspect of the invention, a substance delivery system is designed for mounting to a mammalian face to facilitate delivery of a desired substance into proximity with a mammalian eye. The substance delivery system comprises a shield having a perimeter region configured to lie adjacent the mammalian face about the mammalian eye. A substance delivery element is connected to the shield and at least partially disposed intermediate the shield and the mammalian eye when the perimeter region is disposed adjacent the mammalian face.

Other principle features and advantages of the invention will become apparent to those skilled in the art upon review of the following drawings and detailed description.

BRIEF DESCRIPTION OF THE DRAWINGS

The invention will hereafter be described with reference to the accompanying drawings, wherein like reference numerals denote like elements.

FIG. 5 is another embodiment of the membrane shield; and

FIG. 6 is a cross-sectional view taken generally along line 6—6 of FIG. 5.

DETAILED DESCRIPTION OF THE PREFERRED EMBODIMENTS

Figure 1:
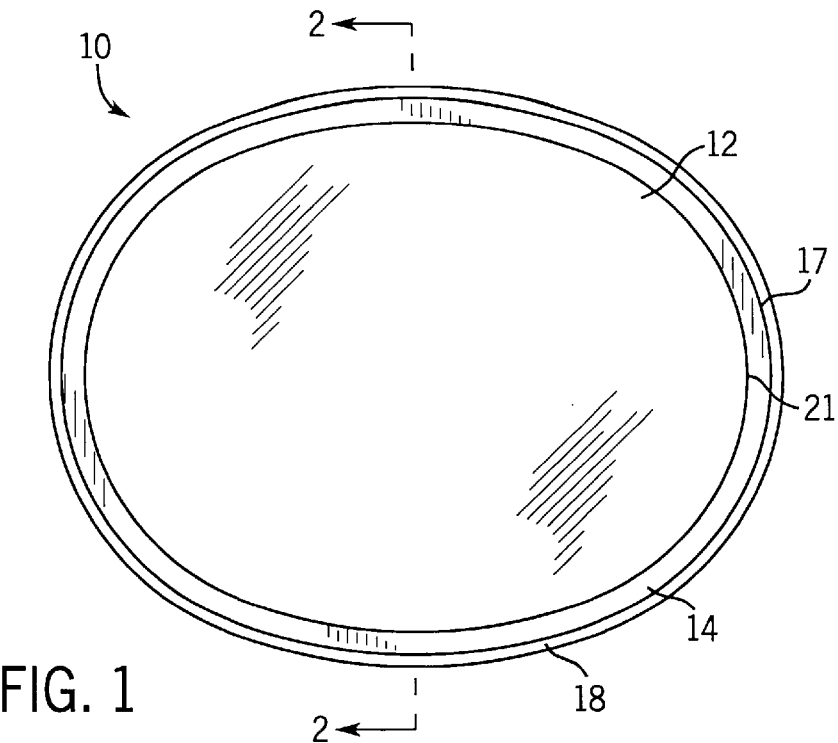
FIG. 1 is a front view of a membrane shield, according to a preferred embodiment of the invention.
Figure 2:
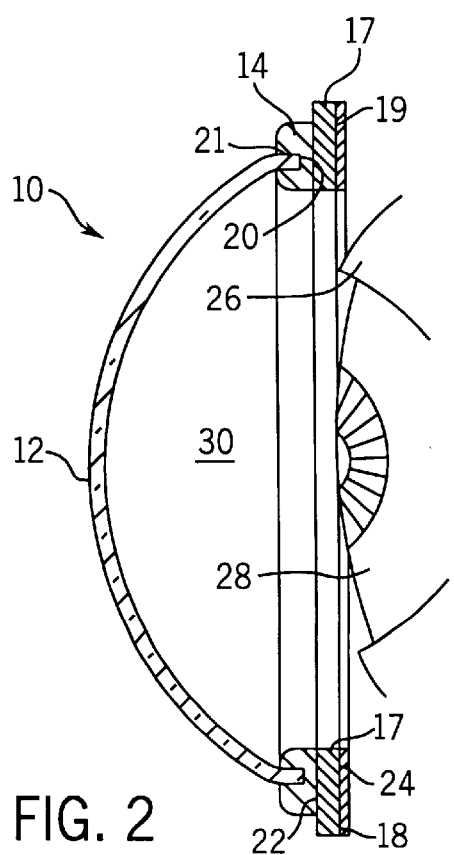
FIG. 2 is a cross-sectional view taken generally along line 2—2 of FIG. 1.

Referring to FIGS. 1 and 2, membrane shield 10, according to a preferred embodiment of the invention, is illustrated.

Membrane shield 10 is designed to protect the eye from dehydration and from particles such as dust and bacteria. Membrane shield 10 includes a central window 12, a base 14, a collar 17 adjoining base 14 and an adhesive 18 for attaching membrane shield 10 to the face of a mammal, such as a human. Additionally, a removable backing 19, such as a wax paper backing, is adhered by adhesive 18 until membrane shield 10 is ready for application to the wearer's face.

Central window 12 has a base rim or perimeter region 20 which is attached to base 14 by, for instance, being integrally formed with base 14 or sealed thereto within a groove 21. Central window 12 may be oblong, e.g., oval, or round in shape, and preferably is made of a transparent material that enables the wearer to see therethrough. The material may be a clear plastic or polycarbonite. The plastic can be a rigid plastic, a flexible plastic or a plastic film, such as HANDI WRAP™ plastic film sold by DowBrands L. P. located in Indianapolis, Ind. In the preferred embodiment, central window 12 is designed with a span or diameter of approximately one to two inches. The material should be impermeable to the passage of water vapor therethrough to ensure moisture does not escape from the wearer's eye.

Collar 17 can be integrally formed with base 14, or it can be a separate layer having a front surface 22 connected with base 14 and a back surface 24 for receiving adhesive 18. Preferably, collar 17 extends radially outward from base 14 and is made of a flexible material. Specifically, the material for the collar 17 can be an impermeable or semi-permeable plastic, cloth or tape, such as SURGICAL PAPER TAPE™, tape product distributed by 3M Corporation, ELASTOPLAST™, or FLEXZAN™, distributed by Dow Hickman Co. For most applications, however, both base 14 and collar 17 should be made of a material that is impermeable to the passage of water vapor therethrough. Thus, central window 12 in combination with base 14 and collar 17 provide a barrier that restricts the ingress of bacteria to the eye and the egress of moisture from the eye. When removable backing 19 is peeled from adhesive 18, collar 17 and adhesive 18 are pressed against a face 26 of a wearer about an eye 28 of the wearer to form a sealed cavity 30 over eye 28.

Figure 3:
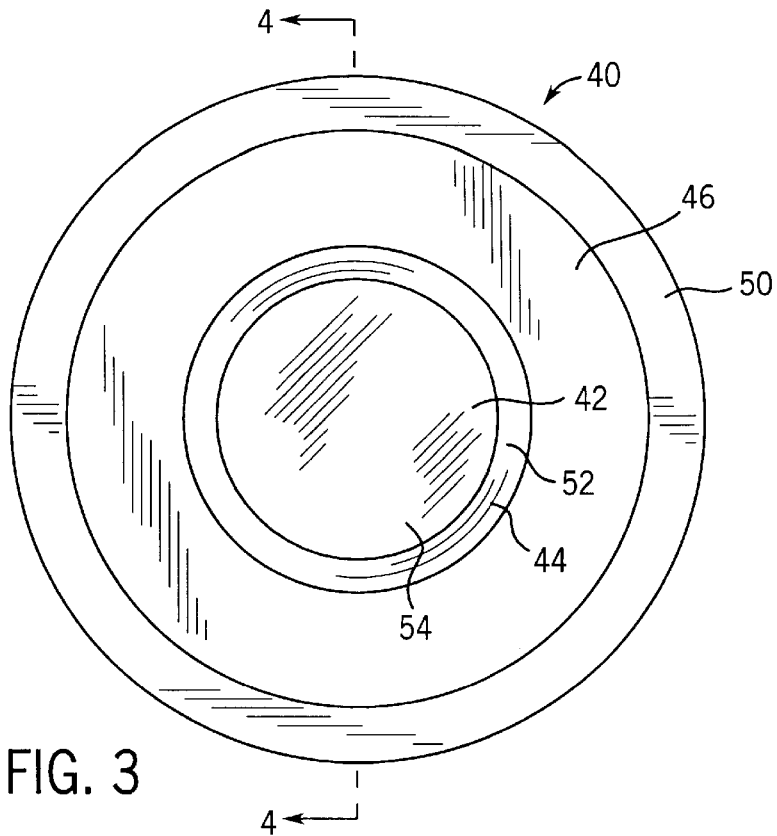
FIG. 3 is an alternate embodiment of the membrane shield illustrated in FIG. 1.
Figure 4:
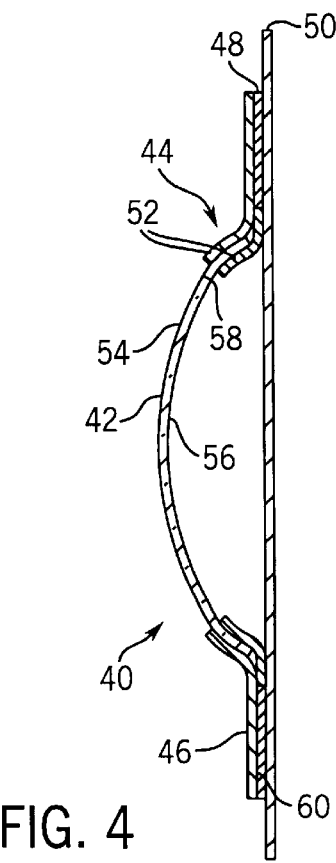
FIG. 4 is a cross-sectional view taken generally along line 4—4 of FIG. 3.

Referring generally to FIGS. 3 and 4, an alternate embodiment of the invention is illustrated. A membrane shield 40, according to an alternate embodiment of the invention, comprises a window 42, a perimeter region 44, a collar 46, an adhesive layer 48 and a backing layer 50.

As described above, window 42 can be formed from a variety of materials, but it is preferably formed from a moisture impermeable transparent material. For example, window 42 can be formed from rigid plastic, flexible plastic or plastic film.

Collar 46 is preferably a flexible material that extends radially outwardly from perimeter region 44 and may be integrally formed with perimeter region 44 or attached thereto by, for instance, an adhesive 52. Collar 46 can be formed of a variety of materials and for most applications it is preferred that the material be impermeable to the passage of water vapor. For example, a variety of plastics or paper materials can be used. However, with paper materials, it often is necessary to use paper coated with wax, polypropylene or polyethylene to render the material impermeable to the passage of moisture.

Adhesive layer 48 is disposed on a contact surface 60 of collar 46 that would be disposed adjacent the wearer's face when membrane shield 40 is adhered about a wearer's eye.

Adhesive layer 48 is preferably a hypoallergenic adhesive that can be applied against the skin of a mammalian wearer, typically a human. In some applications, it is preferred that the adhesive layer 48 comprises a gel, either alone or combined with a conventional adhesive, such as that used on surgical tape. For example, the gel can be applied to a radially inner portion of collar 46, and the conventional adhesive can be applied to a radially outer portion of the collar. One exemplary adhesive layer is petroleum jelly which provides both adhesion and a water vapor impermeable boundary between membrane shield 40 and the face of the wearer.

Furthermore, in many applications it is preferred that central window 12 or window 42 be formed as a lens. Window 42, for example, can be contoured as a lens to improve the vision of the wearer, as conventionally done with corrective glasses. If, for instance, the wearer normally requires reading glasses, eye shields without lenses might prohibit the wearer from reading during the evening. However, central window 12 or window 42 can readily be fashioned to correct vision disorders, such as farsightedness or nearsightedness. Also, as with normal corrective glasses, central window 12 and window 42 can be formed as bifocal lenses.

Referring generally to FIGS. 5 and 6, an alternate embodiment of the invention is illustrated. A substance delivery system 64, according to one embodiment of the present invention, includes a shield 66 mountable to a mammalian face, such as a human face. The system 64 is designed for delivering a desired substance into proximity with a mammalian eye. Substance delivery system 64 is positioned over the mammalian eye similiarly to that illustrated in FIG. 2 during use.

Shield 66 includes a perimeter portion 68 configured to lie adjacent the mammalian face and hold shield 66 over the mammalian eye. In the preferred embodiment, perimeter portion 68 comprises an attachment collar 70 which typically is a flexible sheet that may be pressed along the contours of an individual's face about an eye. Preferably, a window 72 is connected to attachment collar 70. In one exemplary embodiment of the invention, best illustrated in FIG. 6, window 72 includes an interior surface 74, an exterior surface 76 and a perimeter region 78. Attachment collar 70 is connected to perimeter region 78 and extends outwardly therefrom. Attachment collar 70 may be connected to window 72, for example, by an adhesive 80 or by integral formation therewith.

Attachment collar 70 and window 72 may be made from a variety of materials. In most applications, however, window 72 is a generally transparent material, such as a flexible or rigid plastic, as described above. Window 72 may form a cavity 81 that is disposed over the eye during use. Additionally, window 72 may be formed as a lens to provide desired correction or adjustment of the vision of the individual wearing shield 66. To further promote clarity of vision, it may be desirable to provide an anti-fogging compound, such as a conventional silicon-based anti-fogging compound, to window 72 along, for instance, interior surface 74.

Substance delivery system 64 further includes a substance delivery element 84. Substance delivery element 84 is connected to shield 66 and at least partially disposed intermediate shield 66 and the eye of the individual when shield 66, and specifically, perimeter portion 68 is placed adjacent the face of the individual. For example, substance delivery element 84, may be adhered to interior surface 74 of window 72 by a suitable adhesive 86, as illustrated in FIGS. 5 and 6. In the preferred embodiment, substance delivery element 84 comprises an absorbent pad 88, such as a sponge or a paper-based pad, readily able to absorb a desired substance 90 that is typically in the form of a liquid.

Desired substance 90 may comprise a variety of substances helpful in providing moisture and/or medication to the eye of an individual wearing substance delivery system 64 over his or her eye. Exemplary desired substances include artificial tears, antibiotics, anti-inflammatory medications and glaucoma medications. When shield 66 is placed over an individual's eye, the liquid moisturizer and/or medication evaporates with the help of the individual's body temperature. This provides a moist, medicated environment in proximity to the eye, and this environment is held within the cavity 81 formed between window 72 and the eye of the individual. Long term exposure to the ambient medication held within this cavity can be used to treat various ailments of the eye.

In the illustrated embodiment, shield 66 is held in place about the individuals eye by an adhesive layer 92 applied to attachment collar 70 along its attachment surface 93 disposed adjacent the individual's face. As described above, adhesive layer 92 may also comprise a gel, such as petroleum jelly, to facilitate a seal between attachment collar 70 and the face of the individual wearing substance delivery system 64. Often, it is desirable to form both window 72 and attachment collar 70 from materials impermeable to the passage of water vapor, thereby maintaining the moist and/or medicated environment over the eye of the individual. Furthermore, a peelable backing layer 94 may be placed over adhesive layer 92 to protect it prior to use. An individual simply peels backing layer 94 away from attachment collar 70 and adhesive 92 when substance delivery system 64 is applied to his or her face.

It will be understood that the foregoing description is of preferred exemplary embodiments of this invention and that the invention is not limited to the specific forms shown. For example, the window and collar can be made in a variety of shapes, sizes and contoured configurations to facilitate ease of use by the wearer. The collar, for instance, can be round, oblong or have protruding flaps to promote adhesion to the wearer's face. Additionally, the collar can be made water vapor impermeable through the use of an impermeable adhesive layer rather than an impermeable collar material. These and other modifications may be made in design and arrangement of the elements without departing from the scope of the invention as expressed in the appended claims.

What is claimed is:

1. A delivery system mountable to a mammalian face for delivering a desired substance to a mammalian eye over an extended period of time, comprising:

a substantially transparent window having an interior surface, an exterior surface and a base perimeter region;

a collar connected to the base perimeter region, the collar extending outwardly from the base perimeter region to facilitate mounting to the mammalian face; and an absorbent pad disposed adjacent the interior surface at a position spaced from the mammalian eye when the delivery system is mounted to the mammalian face, the absorbent pad being sufficiently porous to absorb a desired substance prior to mounting the delivery system over the mammalian eye.

2. The delivery system as recited in claim 1, further comprising an adhesive layer disposed on the collar to facilitate attachment of the delivery system to the mammalian face about the mammalian eye.

3. The delivery system as recited in claim 2, further comprising a removable backing layer adhered to the adhesive layer.

4. The delivery system as recited in claim 3, wherein the collar includes a flexible plastic material integrally molded with the window.

5. The delivery system as recited in claim 2, wherein the adhesive layer includes a gel.

6. The delivery system as recited in claim 5, wherein the gel comprises petroleum jelly.

7. The delivery system as recited in claim 1, wherein the window is a generally transparent plastic material.

8. The delivery system as recited in claim 1, wherein the window comprises a lens.

9. The delivery system as recited in claim 7, wherein the generally transparent plastic material comprises a rigid material.

10. A moisture shield for application to a mammalian face to retain moisture in a mammalian eye, comprising:

a substantially transparent window having an interior surface, an exterior surface and a base perimeter region;

an attachment collar connected to and extending outwardly from the base perimeter region;

an adhesive layer disposed on the attachment collar to facilitate attachment of the moisture shield to the mammalian face to create a cavity about the mammalian eye; and a substance delivery element disposed at least partially between the interior surface and the mammalian eye when the moisture shield is attached to the mammalian face to deliver a substance throughout the cavity.

11. The moisture shield as recited in claim 10, wherein the attachment collar is formed as a unitary structure with the window.

12. The moisture shield as recited in claim 10, further comprising a removable backing layer adhered to the adhesive layer.

13. The moisture shield as recited in claim 10, wherein the adhesive layer includes a gel.

14. The moisture shield as recited in claim 10, wherein the window is a transparent plastic material.

15. The moisture shield as recited in claim 10, wherein the substance delivery element comprises an absorbent pad.

16. The moisture shield as recited in claim 15, wherein the absorbent pad is adhered to the interior surface.

17. The moisture shield as recited in claim 10, further comprising a liquid substance at least temporarily held by the substance delivery element, wherein the liquid substance is able to evaporate to create a moist environment contained within a cavity proximate the mammalian eye.

18. The moisture shield as recited in claim 17, wherein the liquid substance comprises a medicinal substance.

19. The moisture shield as recited in claim 17, wherein the liquid substance comprises an artificial tear substance.

20. A substance delivery system mountable to a mammalian face for delivering a desired substance into proximity with a mammalian eye, comprising:

a clear, plastic shield having a perimeter portion, the perimeter portion being affixed to a collar that is configured to lie adjacent the mammalian face to create an enclosed cavity about the mammalian eye;

a substance delivery element connected to the shield and disposed at least partially between an interior surface of the shield and the mammalian eye when the collar is disposed adjacent the mammalian face; and a substance carried by the substance delivery element for dissemination through the enclosed cavity.

\* \* \* \* \*